United States Patent
Müller-Schulte (12)

(10) Patent No.: US 6,204,033 B1
(45) Date of Patent: Mar. 20, 2001

(54) PREPARATION OF POLYVINYL ALCOHOL-BASED MAGNETIC PARTICLES FOR BINDING BIOMOLECULES

(76) Inventor: Detlef Müller-Schulte, Steppenbergallee 167, D-52074 Aachen (DE)

(*) Notice: Subject to any disclaimer, the term of this patent is extended or adjusted under 35 U.S.C. 154(b) by 0 days.

(21) Appl. No.: 09/011,667

(22) PCT Filed: Jun. 3, 1996

(86) PCT No.: PCT/EP96/02398

§ 371 Date: Jun. 25, 1998

§ 102(e) Date: Jun. 25, 1998

(87) PCT Pub. No.: WO97/04862

PCT Pub. Date: Feb. 13, 1997

(30) Foreign Application Priority Data

Jul. 31, 1995 (DE) .............................................. 195 28 029

(51) Int. Cl.[7] .................... C12N 11/06; G01N 33/549; G01N 33/53; C07K 17/06; C07K 17/08
(52) U.S. Cl. ........................... 435/181; 435/4; 435/6; 435/7.1; 435/176; 435/180; 436/531; 436/532; 530/402; 530/413; 530/815; 530/816; 536/25.4
(58) Field of Search ............................ 435/174, 176, 435/177, 180, 181, 182, 4, 6, 7.1; 436/531, 532; 530/402, 413, 815, 816; 536/25.4

(56) References Cited

U.S. PATENT DOCUMENTS

| | | | |
|---|---|---|---|
| 2,870,740 | 1/1959 | Vogt | 120/1 |
| 4,070,246 | 1/1978 | Kennedy et al. | 428/378 |
| 4,106,488 | 8/1978 | Gordon | 424/1.37 |
| 4,115,534 | 9/1978 | Ithakissios | 436/500 |
| 4,136,683 | 1/1979 | Gordon | 424/9.32 |
| 4,169,804 | 10/1979 | Yapel, Jr. | 252/62.53 |
| 4,230,685 | 10/1980 | Senyei et al. | 436/526 |
| 4,247,406 | 1/1981 | Widder et al. | 424/484 |
| 4,267,234 | 5/1981 | Rembaum | 428/403 |
| 4,345,588 | 8/1982 | Widder et al. | 600/12 |
| 4,357,259 | 11/1982 | Senyei et al. | 264/4.3 |
| 4,452,773 | 6/1984 | Molday | 424/1.37 |
| 4,628,037 | 12/1986 | Chagnon et al. | 436/526 |
| 4,647,447 | 3/1987 | Gries et al. | 424/9.36 |
| 4,654,267 | 3/1987 | Ugelstad et al. | 428/407 |
| 4,735,796 | 4/1988 | Gordon | 424/9.32 |
| 4,827,945 | 5/1989 | Groman et al. | 424/9.32 |
| 4,861,705 | 8/1989 | Margel | 435/2 |

FOREIGN PATENT DOCUMENTS

| | | |
|---|---|---|
| 2157902 | 8/1980 | (DE) . |
| 3811042 | 10/1989 | (DE) . |
| 4127657 | 2/1993 | (DE) . |
| 1439031 | 6/1976 | (GB) . |
| 9007380 | 7/1990 | (WO) . |

OTHER PUBLICATIONS

Haukanes et al., Application of Magnetic Beads in Bioassays, *Bio/technology* 11: 60–63, 1993.

Kondo et al., Development and application of thermo–sensitive magnetic immunomicrospheres for antibody purification, *Applied Microbiology and Biotechnology* 41: 99–105, 1994.

Shinkai et al., Preparation of Fine Magnetic Particles and Application for Enzyme Immobilization, *Biocatalysis* 5: 61–69, 1991.

*Primary Examiner*—David M. Naff
(74) *Attorney, Agent, or Firm*—D. Peter Hochberg; Katherine R. Vieyra; William H. Holt

(57) ABSTRACT

Spherically shaped polyvinyl alcohol (PVAL) polymer particles are prepared encapsulating a magnetic colloid that provides the particles with magnetic properties for use in binding biomolecules. The particles have a size of 1–10 μm that makes them particularly suitable for use in cell separation/sorting, cleaning biosubstances in suspension and diagnostic assays. The particles are prepared by dispersing a magnetic colloid containing a magnetic material such as a ferromagnetic or superparamagnetic substance in an aqueous solution of polyvinyl alcohol containing reactive hydroxyl groups, adding the resultant mixture to an organic phase containing a mixture of at least two emulsifiers, and adding a water-soluble cross-linking agent such as a dialdehyde that reacts with the hydroxyl groups of polyvinyl alcohol to form the polymer particles. The emulsifiers are miscible in the polyvinyl alcohol solution, and at least one emulsifier is semi-hydrophilic and at least one emulsifier is lipophilic. The cross-linking agent may be used in combination with a water-soluble diamine. The polymer particles contain reactive hydroxyl groups and can be provided with spacer molecules to which biomolecules such as antibodies, peptides, proteins, enzymes, streptavidin, avidin, oligonucleotides, oligosaccharides or DNA can be coupled. Vinyl monomers having one or more functional groups such as carboxyl, hydroxyl, amino, aldehyde or oxirane may be grafted to the polymer particles by radical polymerization under the catalytic effect of cerium (IV).

14 Claims, No Drawings

PREPARATION OF POLYVINYL ALCOHOL-BASED MAGNETIC PARTICLES FOR BINDING BIOMOLECULES

BACKGROUND OF THE INVENTION

1. Field of the Invention.

The present invention relates to a process applied for the production of spherically shaped polymer particles (beads) on the basis of polyvinyl alcohol (PVAL) in which a magnetic colloid has been encapsulated that lends the polymer beads magnetic properties and enables these to bind biomolecules or cells.

2. Description of the Related Art.

In recent years, magnetic polymer beads have been used mainly in biochemistry and medicine to separate cells, proteins and nucleic acids. On account of their magnetic properties, they can also be used as transport systems for certain drugs in certain parts of the body. The use of magnetic beads has great practical advantages over conventional separation systems since the magnetic particles, which usually take the form of fine suspensions or emulsions, can be separated from the mixture by means of magnetic forces. This separation technique dispenses with normal centrifugation. The magnetic fractions can also be separated within one minute and are thus enormoursly time-saving compared to normal chromatographic column separation techniques. A vital part of the aforementioned technique is the time-consuming equilibration and elution processes which can practically be eliminated with the magnetic bead technique. A further important advantage of the magnetic bead technique is the manner of the reaction kinetics. Packing materials with particle sizes of 50–100 $\mu$m are usually used in column chromatography. However, since the separation capacities are often inadequate for such particle sizes, there is an increasing tendency to use particle sizes of <50 $\mu$m and even <10 $\mu$m. In order to withstand the high pressures generated during the passage through the column, such media are practically no longer porous. This is the reason why a change had to be made in practice from the transparent plastic or glass columns to pressure-resistant steel columns. The powerful pump systems needed there are a further disadvantage of today's column chromatography technique. These drawbacks, which are eventually due to inadequate reaction kinetics, can be completely avoided through the use of the magnetic bead technology.

Through the use of finely dispersed PVAL particles with a particle size of 1–10 $\mu$m, preferably 1–4 $\mu$m, the particles remain in suspension for a number of hours so that the reaction kinetics correspond to those of a quasi-homogeneous solution. As a result of this stable suspension, stirring or shaking can also be dispensed with in most cases.

Processes to produce iron-dextrane microparticles are described in the U.S. Pat. No. 4,452,773. 30–40 nm large colloid iron oxide particles in which dextrane has been absorbed are obtained by mixing an Fe(II) and Fe(III) saline solution in the presence of a defined amount of dextrane and subsequently adding alkali. A similar process forms the basis of the PCT application WO 90/07380. Dextrane is added to Fe(II) and Fe(III) saline solutions and treated at 40° C. before being titrated with NaOH to produce superparamagnetic particles with a size of 40–100 nm. The disadvantage of both process is that separation is only possible by means of a high gradient magnetic field because of the fineness of the particles. This high gradient magnetic field is generated by a separating column densely packed with steel wool or similar microparticle substances which is placed between the pole shoes of two strong electromagnets or hand magnets. The particles are separated by passing the suspension through the packed separating column. A separation of such colloids is not possible with normal hand magnets. Therefore, there are in principle hardly any experimental differences between common chromatography techniques. A further disadvantage of the aforementioned process of production is that no uniform particle size can be obtained by the actual production process. This is only possible through a fractionated magnetic separation. Furthermore, detection of these magnetic particles is also complicated by the fact that the particles are no longer visible under a light-optical microscope. In a further process which forms the basis of U.S. Pat. No. 4,070,246, magnetic particles are obtained by converting p-aminobenzoic acid and an aldehyde through the addition of a ferromagnetic powder. The production of defined beads which are normally required for diagnostic tests, is not possible with this process. It is also not possible to chemically couple biomolecules to this carrier. The same applies to the process described in U.S. Pat. Nos. 4,106,448, 4,136,683 and 4,735,796 in which magnetic particles are encapsulated in dextrane for diagnostics and tumour therapy. The covalent coupling of biomolecules of the aforementioned process is also not described. U.S. Pat. No. 4,647,447 describes the production of ferromagnetic particles for NMR diagnostics. This process starts either with Fe(I)/Fe(III) saline solutions or directly with microparticle ferrites which are converted to magnetic suspensions in the presence of a complexing agent in the form of serum albumin, polysaccharides, dextran or dextrin. Other ferromagnetic particles which are encapsulated in a silane matrix are dealt with in U.S. Pat. No. 4,628,037. Superparamagnetic iron oxide, described in U.S. Pat. No. 4,827,945, is also used as contrast medium in NMR diagnostics. Coated magnetic particles can be produced with these substances through precipitation of Fe(II)/Fe(III) saline solutions by means of bases in the presence of serum albumin, polypetides or polysaccharides. The magnetic particles can be targeted into certain areas of the body by coupling specific antibodies to the matrix. The production of iron oxides through the precipitation of iron salts in the presence of dextranes or polyglutaraldehydes, for example, forms the basis of U.S. Pat. No. 4,267,234. All the aforementioned processes and products have one thing in common, namely, the ferromagnetic or superparamagnetic particles are only produced through the precipitation of a saline solution, which assumes a certain molecular ratio of Fe(II) and Fe(III) salts in the presence of a complexing or coating agent. The particles described display a rather wide range of particle sizes. Defined drop or spherical particles cannot be produced with the aforementioned processes. The materials described display an amorphous-like geometric structure. On account of their fineness, which is usually in the nm range, they are primarily suitable as a contrast medium for NMR diagnostics or as a cell marker. Moreover, the separation of the magnetic fractions is not usually possible with a simply hand magnet, such as is advantageous for fast diagnostic tests or affinity chromatography separations.

The preparation of magnetic albumin or protein microparticles coated with specific coupling agents which can be used for virus and cell separations as well as diagnostic tests, is described in U.S. Pat. Nos. 4,345,588; 4,169,804; 4,115, 534; 4,230,685; 4,247,406 and 4,357,259.

Magnetic particles with a defined bead-shape structure are known from U.S. Pat. No. 4,861,705. The subject matter of the aforementioned patent are agarose polyaldehyde composite particles which are produced through a suspension of the polymer phase in an oil phase. Magnetic polymer particles with a particle size of 40–1000 µm are obtained by admixing a ferrofluid, by definition a very fine superparamagnetic aqueous iron oxide colloid, to the polymer phase.

Perfectly bead-shaped particles are described in U.S. Pat. No. 4,654,267. The process differs fundamentally from the aforementioned in that polyacrylates or polystyrene, which is initially radically polymerised to bead-shaped particles by means of suspension polymerisation, is used as a matrix. The particles are then swelled in an organic phase under defined conditions. This is followed by an incubation of the polymer particles in an Fe(II)/Fe(III) saline solution that is oxidised to superparamagnetic iron oxide using ammonia once the particles have diffused. This process produces spherical particles with a particle size of between 0.5 and 20 µm. The process itself is technically very complicated. Apart from the use of highly toxic substances, between 10 and 30 hours are required to prepare the basic matrix. Moreover, additional nitro, nitroso or amino groups are needed which are introduced into the polymer matrix in an additional preparation stage to guarantee an adequate absorption of the Fe salts. The great disadvantage of the particle described here is the basic polymer, polystyrene. Polystyrene is a very hydrophobic material with a strong tendency to unspecific absorption when in contact with protein solutions or other biomolecules. This phenomenon is disadvantageous particularly in immunoassays and affinity chromatography separations. The drawbacks of the aforementioned processes in terms of the production costs and effort, particle geometry, magnetic separation behaviour, properties of the polymer matrix or type of coupling process can be avoided by a novel water-in-oil suspension process. The polymer matrix used is polyvinyl alcohol (PVAL), which is suspended and cross-linked as an aqueous solution by stirring in an organic phase that cannot be mixed with water. Examples of such organic phases are generally known from the state-of-the-art in suspension polymerisation. Common vegetable oils are preferably used for the process in accordance with the invention. In order to achieve the desired magnetic properties of the polymer particles, the polymer phase is mixed with a magnetic colloid, e.g. iron oxide powders or ferrofluids, and then suspended in the oil phase. The production of bead-shaped PVAL particles through the suspension of an aqueous polymer solution is described in the Ger. Offen. 41 27 657. Magnetic particles can be produced by adding magnetite powder to the polymer solution. The aforementioned process uses polymer solutions and oil phases which contain no additives in the form of emulsifiers or other surfactants. Because of this, the particle sizes can quite easily be between 50 and 500 µm. The particle sizes are primarily determined by the viscosity of the organic and/or polymer phase in the aforementioned process.

SUMMARY OF THE INVENTION

The object of the present invention is to produce magnetic particles with a particle size in the range of 1–10 µm, preferably between 1–4 µm, which also display a very narrow particle size distribution. Only such particles can be used for cell separation/sorting, cleaning biosubstances in suspension and diagnostic assays. Interestingly, it has been shown that such polymer particles can be obtained by adding certain emulsifier mixtures to the oil phase. The term emulsifier is defined in the following as a general term for all surfactants such as tensides, detergents or suspension stabilisers. Examples of emulsifiers which are suitable as additives for the oil phase include: propylene oxide-ethylene oxide block copolymers, sorbitan fatty acid esters, complex mixed ester of pentaerythritol fatty acid ester with citric acid, polyethylene glycol castor oil derivates, block copolymers of castor oil derivates, polyethylene glycole, modified polyester, polyoxyethylene sorbitan fatty acid ester, polyoxyethylene-polyoxypropylene ethylenediamine block copolymers, polyglycerol derivates, poloxyethylene alcohol derivates, alkylphenylpolyethylene glycol derivates, polyhydroxy fatty acid polyethylene glycol block copolymers, polyethylene glycol ether derivates. Substances of this kind are known on the market under the trade names: Pluronic®, Synperonic®, Tetronic®, Triton®, Arlacel®, Span®, Tween®, Brij®, Renex®, Hypermer®, Lameform®, Dehymuls® or Eumulgin®.

As regards a uniform, bead-shaped polymer particle with the required particle size of 1–10 µm, it could be shown that only a mixture of at least two, preferably three to four surfactants lead to the required particle specification in the oil phase. One condition for the realisation of the required particle size is a corresponding reduction of the interfacial tension of the phases. This is possible by mixing a lipophilic emulsifier component with at least one emulsifier with semi-hydrophile properties, i.e. which is soluble in both oil and water. Examples of emulsifiers which fulfil the latter requirement are: ethylene oxide propylene oxide block copolymer derivates with a mainly ethylene oxide portion, polyethylene glycol hexadecyl ethers, shorter-chain polyoxyethylene sorbitan fatty acid esters, polyethylene glycol or shorter-chain sorbitan fatty acid esters.

DETAILED DESCRIPTION OF THE INVENTION

The concentration of emulsifiers in the oil phase is usually 2–6 vol. %, preferably 3.5–5.0 vol. %. As regards fineness and narrow particle size distribution of the polymer drops, emulsifier mixtures which contain at least two lipophilic components and one semi-hydrophilic emulsifier are most suitable. The concentration of the semi-hydrophilic emulsifier is usually between 15 and 30 vol. % relative to the total amount of emulsifier. The process in accordance with the invention enables not only the fineness of the particles but also the production of bead-shaped particles, which are a precondition for a homogeneous suspension. This permits the exact pipetting required in biochemical and medical analysis/diagnostics.

Apart from the emulsifiers for the oil phase, special surfactants, which are soluble in the aqueous polymer phase, also help improve the quality of the suspension, particularly for polymer solutions with low molecular masses (20,000–80,000). Furthermore, it could be shown that the magnetic colloids added in a solid form are only finely dispersed after the addition of ionic emulsifiers. Examples of such emulsifiers, which can also be used as binary mixtures, are: serum albumin, gelatin, aliphatic and aromatic sulfonic acid derivates, polyethylene glycole, poly-n-vinylpyrrolidone or cellulose acetate butyrate. The quantity of emulsifier used is usually 0.01–2 weight % relative to the polymer phase, whereby the concentration of ionic emulsifiers can be between 0.01 and 0.05 weight %. The influences on the particle size such as stirring speed as well as concentration and viscosity of the two phases, as shown in Ger. Offen. 41 27 657, play only a subordinate role in the process in accordance with the invention on account of the emulsifier additives. In order to obtain the necessary particle size of 1–10 µm, stirring speeds of 1500–2000 rpm are adequate, whereby normal two-bladed propeller mixers are used. The determining influence of the emulsifier on the particle size in the present invention becomes clear from the fact that if the stirring speed is reduced from 2000 to 1300 rpm, the particle size increases from 1–5 µm to 2–8 µm. If the stirring speed is increased from 2000 to 5000 rpm there is practically no change in the particle size. On the other hand, the size of particles produced by the aforementioned process vary between 10 and 80 µm with an analogous change in the stirring speeds. The influence of the viscosities of both the suspension phase and the polymer phase on the particle size observed in the aforementioned patent is also minimal compared to the influence of the emulsifiers in the present invention. Thus, the sizes of PVAL particles only fluctuate between 2 and 8 µm when the viscosity of the polymer phase is changed from 10 to 1000 mPa s in the process in accordance with the invention, and between 50 and 140 µm with the aforementioned process under the same conditions.

In principle, any ferro- or superparamagnetic colloids with a corresponding particle size and which generally have a magnetic saturation of 50–400 Gauss can be used as magnetic particles for encapsulation in the polymer matrix during the suspension cross-linking process.

A further requirement which the magnetic particles have to fulfil is the dispersibility in the aqueous polymer phase. Unlike the process to produce magnetic particles as described in U.S. Pat. No. 4,654,267, which is based on a complicated swelling process with iron salts and subsequent oxidation to magnetic colloids, the magnetic colloids can be dispersed directly in the polymer phase with the present process. During the following suspension in the organic phase the magnetic colloids are then simultaneously encapsulated in the polymer beads. This represents a significant simplified procedure compared to the aforementioned process, and also means enormous time-savings for the production process. Whereas preparation times of 10 to 30 hours are necessary to produce the aforementioned agents on polystyrene basis, the process in accordance with the invention takes only 5 to 30 minutes to produce the basic magnetic particles.

Magnetite with a particle size of 10–200 nm is preferably used as a magnetic colloid, whereby the process in accordance with the invention is not restricted to this type of substances. Such substances are available under the trade names Bayferrox or EMG (Ferrofluidics), for example. Since the production of such colloids is state-of-the-art, the magnetic particles can also be produced according to known processss, e.g. as described by Shinkai et al., Biocatalysis, Vol. 5, 1991, 61, Reimers and Khalafalla, Brit. Pat. 1.439.031 or Kondo et al., Appl. Microbiol. Biotechnol., Vol. 41, 194, 99. The concentrations of colloids in the polymer phase relative to the polymer phase in each case are between 4 and 14 vol. % for those colloids which are already aqueous on account of their production process, and 0.3–2 weight % for solid substances. The magnetic colloids are mixed directly in the polymer phase during production. In order to guarantee a finely dispersed, even distribution of the particles, a short-term mixing of the aqueous dispersion with a high-speed disperser (Ultra-Turrax) and subsequent ultrasonic treatment is of advantage.

The polymer phase required to produce the magnetic particles usually consists of a 2.5–10 weight % PVAL solution. As known from Ger. Offen. 41 27 657, the porosity of the polymer particles is ultimately determined by the polymer coil density, which in turn is determined by the mean molecular mass of the polymers and the concentration. A higher molecular mass and/or lower polymer concentration means a lower coil density and thus increasing porosity. Since the practicality of a test process, particularly during routine diagnostic or analytical processes, depends on the quantity of substances absorbed per quantity of carrier, the porosity plays an important role during magnetic particle production as a co-determining parameter. This is the reason why polymer concentrations of 2.5–5 weight % and molecular masses of >50,000 are preferably used in the materials according to the invention. Polymer particles produced in this manner have a high porosity and a correspondingly high binding capacity, in terms of both the ligands coupled to the matrix and the ligates and biomolecules bound by the ligands. A further factor which affects the porosity and thus the functionality of the magnetic particles, is the choice of cross-linking agent and its concentration. In view of the high loading capacities, the concentrations of the cross-linking agents are chosen so as to guarantee a corresponding porosity together with an adequate dimensional stability. All water-soluble bifunctional compounds capable of reacting with the hydroxyl groups of PVAL can in principle be used as cross-linking agents, e.g. aldehydes, acid chlorides or divinyl sulfone. Glutaraldehyde under an acid catalyst is preferably used as a cross-linking agent since this substance reacts with the polymers within a few minutes to produce firmly cross-linked particles. Between one and two hours reaction time are needed for the other substances. The use of glutaraldehyde also offers the opportunity of extending the cross-linking agent by the length of a diamine chain through the simultaneous addition of a water-soluble diamine, e.g. ethylenediamine or hexamethylenediamine, thus increasing the porosity of the polymer matrix. The concentrations of the cross-linking agent, relative to the aqueous polymer phase, are usually between 0.2 and 1 vol. % and between 2 and 7 vol. % for glutaraldehyde. Glutaraldehyde is often used in the form of a 6–25% aqueous solution. Between 10 and 50 mol %, relative to the amount of glutaraldehyde, are normally used.

To produce the magnetic particles, generally 20–25 times the volumetric quantity of an organic phase, preferably common vegetable oil, are added and the polymer magnetic colloid mixture is then suspended by stirring. The addition of an acid in the case of glutaraldehyde cross-linking is hereby determined by the stability of the magnetic colloid. Some magnetic colloids tend to agglomerate when acid is added. This can be avoided by adding the acid during or at the end of the suspension process. Since the magnetic colloids are already finely dispersed in the polymer matrix at this point in time, agglomeration can be completely avoided. In the case of acid-resistant magnetic colloids, the acid can also be added directly to the polymer phase before the suspension process. The cross-linking agent is added during the suspension process in both cases. Apart from those parameters described above which determine the particle size and geometry, it can be shown that the acid concentration also has a decisive influence on the suspensibility of the magnetic particles. Good suspensibility means that the particles are completely isolated from one another and form no agglomerates whatsoever in an aqueous solution. This property, which is a precondition for a long dispersion half-life of the particles in aqueous solutions, is achieved with an acid concentration of 15–50 vol. % relative to the polymer phase. 1–3 N HCl is preferably used. The dispersion times in the suspension are correspondingly very high for the PVAL particles, between 12 and 48 hours, compared to 2 hours for the polystyrene beads in the U.S. Pat. No. 4,654,267.

The magnetic particles obtained in this manner, whose special advantages are based on such properties as porosity, particle size, magnetic behaviour and chemical functionality, all of which can be adapted by a variety of process parameters, can be used for a number of applications, many of which cannot be done with the other magnetic carriers described above.

On account of the high chemical functionality of the basic polymer PVAL, all activation and coupling processs known from common affinity chromatography media can be used with the process in accordance with the invention. Examples of such activation agents are: BrCN, 2-fluoro-1-methylpyridinium-p-toluenesulfonate, 1,1'-carbonyldiimidazole, epichlorohydrin, hexamethylenediisocyanate or 1-cyano-4-dimethylaminopyridinium-tetrafluoroborate. The corresponding coupling processes for bioligands and biomolecules are state-of-the-art and have been described, amongst others, in Methods in Enzymology, Vol. 135, 1987, edited by K. Mosbach. The coupling processes in the aforementioned U.S. Pat. No. 4,654,267 are, on the other hand, restricted to the activation and coupling of carboxyl groups.

The existing hydroxyl groups of the basic polymers in accordance with the invention described here also offer the opportunity of grafting vinyl monomers onto the polymer matrix. Additional functional molecular chains (spacer molecules) can be introduced by this grafting process. The coupling of the biomolecules to such spacer molecules generally requires the retention of the native structure and thus the biological activity of the coupled biomolecules. Since the biomolecule now no longer makes direct contact with the matrix surface, possible conformation modifications within the biomolecule are prevented. Grafting with vinyl monomers takes place under the catalytic effect of cerium(IV) salts, e.g. cerium(IV) ammonium nitrate or cerium(IV) ammonium sulfate, which act as redox initiators for the radical polymerisation. The cerium(IV) salts are preferably used as 0.03–0.1 molar solutions in 0.5–1 N sulfuric acid or nitric acid. Substances which have functional or reactive groups, for example in the form HO—, HOOC—, $NH_2$—, NCO—, CHO— or oxirane groups, are used as vinyl monomers. With regards to the details of such basically known grafting process, reference is made to the processes described in the disclosure publications Ger. Offen. 21 57 902 and Ger. Offen. 38 11 042. However, the polymer matrices in accordance with the invention presented here differ fundamentally from the aforementioned graft matrix in terms of their physical and chemical structure, properties and applicability. A further difference to the aforementioned grafting process is that the materials in accordance with the invention do not have to be used in a non-oxygen atmosphere, rather the presence of an organic solvent which cannot be mixed with water, e.g. hexane, heptane, cyclohexane or petroleum ether, is adequate to achieve high graft yields. The grafting times can also be reduced by up to 90% compared to the aforementioned processes. The quantities of vinyl monomers used vary between 10 and 50 vol. %, relative to the magnetic particle suspension.

On account of the variety of activation and modification possibilities for the PVAL magnetic particles, a practically unlimited number of biomolecules can be coupled to the matrix. This leads to a wide field of applications, ranging from medical diagnostics to molecular biology analyses. An important application within biosciences is separation according to the principle of affinity. The column technique normally used here involves a complicated experimental set-up, so that practical alternatives are desirable, particularly for smaller, routine separations. The materials in accordance with the invention offer such alternatives since these require only a fraction of the time and experimental equipment needed for normal techniques. All ligands which are in use today in affinity clromatography can in principle be coupled as ligands. Examples here, which also open up interesting prospects from a practical aspect, are: protein A, protein G, heparin, antibodies, serum albumin, gelatin, lysine, concavalin A, oligosaccharides, oligonucleotides or enzymes. The special separations which can be carried out with such affinity matrices are state-of-the-art. We refer to J. of Chromatography, Vol. 510, 1990 for details of the known processes. Apart from the experimental simplification, the special advantage of magnetic particle technology is a significant reduction in the separation times. This is due to the fact that the magnetic particle suspension is a quasi-homogeneous phase which permits reaction kinetics analogous to those of a homogenous solution. This means that separations can be carried out within 2–5 minutes, depending on the batch scale, with no great effort.

A further, interesting field of application for magnetic particle technology is diagnostics, in particular the field of immunoassays. The basic principle is the quantitative detection of specific substances. The quality of the detection is hereby directly linked to the specific isolation of the corresponding substance, be this by chromatography or by binding to a polymer solid. This specific binding is normally carried out by means of an immobilised antibody, which is then photometrically or nephelometrically analysed. The newly developed PVAL media provide an excellent basis for immunoassays. Antibodies against diagnostically relevant antigens are hereby chemically coupled to the magnetic particles. Examples of such antibodies are: anti-insulin, anti-thyroxine, antibody against the thyroid-stimulating hormone (TSH), antibody against the thyroid-binding globulin, anti-cortisone, anti-ferritine, anti-chorionic gonadotropine, anti-carcinogen-embryonic-antigen (CEA), anti-progesterone, anti-testosterone, anti-estradiole, anti-prolactine, anti-human-growth-hormone, anti-digoxine, anti-β2-microglobulin, anti-α2-macroglobulin, anti-vitamin B12, anti-factor VIII or anti-AFP. The incubation times for the antibody-coupled magnetic particles with the substance mixtures is normally 2–5 minutes. Following magnetic separation, the isolated antibody-antigen complexes are photometrically quantitatively detected using known analysis processs. The use of magnetic particle technology means that the incubation times can be reduced by a factor of 10–100 compared to conventional micro-titre plate or column separation processes, such as are described in Ger. Offen. 41 26 436. Apart from antibodies, other substances can be coupled to the magnetic particles and used to detect specific substances. Such a substance is 3-aminophenylboronic acid which is coupled to the PVAL matrix to detect the blood sugar content. In order to immobilize the ligands, the PVAL carrier is activated with diisocyanates in the first stage. It is then converted with the ligand. 15–30 mg 3-aminophenylboronic acid per 100 mg magnetic phase are normally used for the conversion. The blood sugar content is analysed by means of the glycated hemoglobin in the blood, which binds specifically to the boronic acid ligands. Upon subsequent elution of the bound glycated fraction from the matrix it can be quantitatively analysed by means of photometric measurements. The particular advantage compared to earlier test processes is the reduced time effort. This process is thus ideal for routine analyses.

Molecular-biology analyses, which have recently become very popular in the course of new therapeutic and diagnostic processs, are a further field of application for the PVAL magnetic particles.

The high affinity between streptavidin/avidin and biotin is used in a number of analytical processes in molecular biology. Biotinylated biomolecules of any kind, e.g. DNA fragments, oligonucleotides, proteins, antibodies or antigens, can be isolated by coupling streptavidin or avidin to polymer solid phases. The use of the PVAL matrix enables the simple performance of such separations on account of the simple coupling technique in connection with the high suspensibility. Examples of practical applications where the magnetic bead technology could preferably be used are: solid-phase DNA-sequencing, DNA synthesis or polymerase chain reaction (PCR). The PVAL magnetic particles also enable cell separation and labelling through coupling with antibodies which are targeted against certain cell markers, e.g. anti-CD4, anti-CD15, anti-CD35, anti-CD8. We refer to the pertinent literature for further details: Haukanes and Kram, Biotechnology, Vol. 11, 1993, 60.

The invention will be explained in more detail in the following examples.

EXAMPLE 1

A magnetic colloid is produced analogous to the specifications of Kondo et al., Appl. Microbiol. Biotechnology, Vol. 41, 1994, 99–105. 10 ml of the colloid are dispersed in a mixture of 80 ml 10% PVAL solution (mean molecular mass 48,000), 5 ml 2.5% polyvinylpyrrolidone solution, 20 ml 2 N HCl and 0.4 ml 3.5% sodium-dodecylsulfate. Following a 1 minute treatment in an ultrasonic bath (100 W) the mixture is suspended in 2 litres of a normal vegetable oil containing 2% Pluronic 6100, 0.8% Pluronic 6200, 0.4% Dehymuls FCE and 0.6% Dehymuls HRE7 at 20° C. by stirring. The stirring speed is 2000 rpm.

After 10 seconds, 6.4 ml 12% glutaraldehyde solution is added. Stirring continues for a further 20 seconds. The suspension is then centrifuged at 5000×g for 30 seconds and the oil phase decanted. The remaining suspension is rinsed once with approx. 300 ml n-hexane and once with approx. 300 ml methyl ethyl ketone. The magnetic suspension obtained is dispersed in approx. 400 ml water/methanol 1:1 (v/v) and then centrifuged. The magnetic fraction is then washed ten times by means of dispersion in approx. 400 ml water with a centrifuge step between each washing.

Magnetic particles with a size distribution of 2–4 $\mu$m and an iron content of 7% are obtained. (All % figures here and in the following are in vol. %, for fluid substances, and weight % for solid substances).

EXAMPLE 2

5 ml of magnetic colloid according to Example 1 are dispersed in 40 ml PVAL phase according to Example 1 and then suspended by mixing in 880 ml normal vegetable oil (stirring speed 2000 rpm), in which 1.5% Pluronic 8100, 0.4% Pluronic 6200 and 0.4% Dehymuls FCE have been dissolved.

4% of a 25% glutaraldehyde solution are then added. The suspension is stirred for a further 10 seconds. After 10 minutes the suspension is centrifuged and washed in accordance with Example 1 using methanol/water, n-hexane and methyl ethyl ketone. Magnetic particles with a size of 1–3 $\mu$m are obtained. The iron oxide content is 7.3%.

EXAMPLE 3

4 ml of Ferrofluidics EMG 807 are dispersed in 100 ml 5% PVAL solution (mean molecular mass 224.000). The dispersion is treated for 5 minutes in an ultrasonic bath and then suspended by stirring in 2300 ml vegetable oil containing 2% Arlacel 83, 0.8% Tween 85 and 0.4% Dehymuls FCE (stirring speed 1800 rpm).

After 5 seconds, 25 ml of 2.5 N HCl are added and 7 ml of 12% glutaraldehyde solution after a further 5 seconds. Stirring continues for a further 10 seconds. The suspension is centrifuged and washed after 10 minutes as described in Example 1.

Magnetic particles with a particle size of 2–5 $\mu$m and an iron oxide content of 24.6% are obtained.

EXAMPLE 4

180 mg Bayferrox PR 5044 N iron oxide pigment are added to 20 ml 7% PVAL solution (mean molecular mass 88.000) which contains 0.01% polystyrene sulfonic acid and 0.05% polyethylene glycol 1000 and dispersed for one minutes at 20.000 rpm using a dispersion tool (Ultra-Turrax). This is followed by two treatments in an ultrasonic bath for two minutes each.

The mixture is subsequently dispersed under stirring (stirring speed 2000 rpm) in 460 ml vegetable oil which contains 1.9% Arlacel 83, 0.4% Tween 20, 0.3% Dehymuls FCE and 1% Dehymuls HRE 7.

After 10 seconds, 0.8 ml of a 25% glutaraldehyde solution is added followed after 5 seconds by addition of 8 ml 1 N HCl. Stirring of the suspension is continued for another 10 seconds.

After 10 minutes the fraction is isolated and washed according to Example 1.

Magnetic particles with a size of 2–4 $\mu$m and an iron content of 12.3% are formed.

EXAMPLE 5

50 mg Bayferrox 318 M are dispersed in 10 ml of a mixture containing 5% PVAL (mean molecular mass 224.000), 0.01% sodium dodecyl sulfate and 0.1% polyethylene glycol 1000 using an Ultra-Turrax (20.000 rpm). Subequently, the polymer phase is dispersed under stirring (1800 rpm) in 250 ml vegatable oil containing 2.2% Span 80, 0.4% Dehymuls FCE and 0.4% Pluronic 6200.

After 5 seconds, 10 ml 1 N HCl and after 10 further seconds 0.6 ml 25% glutaraldehyde solution is added. Stirring is continued for another 10 seconds. After 5 minutes the suspension is centrifuged. The collected fraction is washed according to Example 1.

Magnetic particles with a size of 3–6 $\mu$m and an iron oxide content of 10.2% are formed.

EXAMPLE 6

6.4 ml magnetic colloid as described in Example 1 is dispersed in a mixture containing 50 ml 4% PVAL (mean molecular mass 103.000), 0.1% bovine serum albumin and 0.5% polyethylene glycol 1000. The dispersion is treated for 5 minutes in an ultrasonic bath and subsequently suspended (stirring speed 2000 rpm) in 1100 ml vegetable oil which contains 1.8% Span 85, 0.8% Synperonic PL 61, 0.8% Tetronic 901 and 0.4% Dehymuls FCE.

After 120 seconds, 4 ml 12% glutaraldehyde solution is added followed after 5 seconds by an addition of 12.5 ml 2.5 N HCl. Stirring is continued for another 10 seconds, followed by centrifugation and further washing according to Example 1.

Magnetic particles with a beads size of 1–3 $\mu$m and an iron oxide content of 8.3% are obtained.

EXAMPLE 7

13 ml Ferrofluidics EMG 507 are mixed to 100 ml 3.5% PVAL solution (mean molecular mass 224.000) containing 20% 3 N HCl; the mixture is treated for 0.5 minutes in an ultrasonic bath. The magnetite-polymer-phase is suspended under stirring (stirring speed 2000 rpm) in 2.3 liters vegetable oil which contains 1.8% Pluronic 6100, 0.2% Pluronic 6200, 0.2% Hypermer A60 and 1.8% Dehymuls HRE 7.

After 10 seconds 8 ml 12% glutaraldehyde solution is added and stirring is continued for 15 seconds After 10 minutes the suspension is centrifuged and washed according to Example 1. The collected beads have a size of 1–2 $\mu$m and exhibit an iron oxide content of 14.2%.

EXAMPLE 8

100 ml 7.5% PVAL solution (mean molecular mass 88.000), in which 0.05% gelatin is dissolved, are mixed with 12.5 ml Ferrofluidics EMG 707 and sonicated for 3 minutes in an ultrasonic bath. The mixture is subsequently suspended under stirring (stirring speed 2000 rpm) in 2.5 liters vegetable oil which contains 1% Arlacel 83, 0.4% Pluronic 6100, 0.2% Brij 52 and 0.4% Tween 60.

After 10 seconds 4 ml 12% glutaraldehyde solution and after further 5 seconds 26.5 ml 1 N HCl is added. Stirring is continued for further 15 seconds. After 15 minutes the suspension is centrifuged according Example 1.

Magnetic particles with a size of 2–4 $\mu$m and an iron oxide content of 26% are obtained.

EXAMPLE 9

10 ml 7.5% PVAL solution (mean molecular mass 103.000) are adjusted to pH 9.5 with 0.5 N NaOH and 75 $\mu$l divinyl sulfone are added. Susequently 1.2 ml magnetic colloid according to Example 1 are dispersed in the aqueous phase. After 3 minutes treatment in an ultrasonic bath, the mixture is suspended under stirring (stirring speed 2000) in 220 ml vegetable oil in which 2% Span 60, 0.4 Tween 80 and 0.4% Dehymuls FCE is dissolved. Stirring is continued for another 30 seconds after which the suspension is left for 60 minutes at room temperature.

The suspension is washed as described in Example 1. Beads with a size of 4–8 $\mu$m and an iron oxide content of 7.7% are obtained.

EXAMPLE 10

5 ml Ferrofluidics EMG 707 are charged to 100 ml 3.5% PVAL solution (mean molecular mass 224.000), in which 40% 1 N HCl and 0.015% sodium dodecyl sulfate is dissolved; the mixture is sonicated for one minutes in an ultrasonic bath. The polymer phase is subsequently suspended under stirring (stirring speed 2000) for 10 seconds in 2.3 liters vegetable oil which contains 1% Arlacel 83, 1% Pluronic 6100, 0.8% Tween 80 and 2% Dehymuls HRE 7

After 10 seconds, 6 ml 25% glutaraldehyde solution are added and stirring continued for another 10 seconds. After 10 minutes the suspension is centrifuged and washed according to Example 1. Magnetic particles with a size of 2–4 $\mu$m and an iron oxide content of 24% are obtained.

EXAMPLE 11

14.5 ml magnetic colloid according to Example 1 are dispersed in 100 ml polymer phase which contains 4% PVAL (mean molecular mass 224.000) and 0.1% bovine serum albumin The mixture is treated for one minutes in an ultrasonic bath. Afterwards the dispersion is suspended for 15 seconds under stirring (stirring speed 2000) in 2.5 liters vegetable oil in which 3.8% Pluronic 3100, 0.8% Pluronic 6200 and 1.5% Tetronic 304 is dissolved.

Then 7.5 ml 12% glutaraldehyde solution and after further 10 seconds 25 ml 3 N HCl are added; stirring is continued for another 10 seconds. After 10 minutes the suspension is washed and prepared further according to Example 1.

Magnetic particles with a size of 1–2 $\mu$m and an iron oxide content of 9.5% are obtained.

EXAMPLE 12

50 ml polymer phase containing 5% PVAL (mean molecular mass 224.000), 0.5% polyethylene gylcol 3350 and 12% Ferrofluidics EMG 707 are suspended for 10 seconds under stirring (stirring speed 1800) in 1200 ml vegetable oil in which 2.2% Arlacel 80, 0.8% Span 85 and 0.8% Triton CF10 are dissolved.

In 5 sec intervals 4 ml 25% glutaraldehyde solution and 25 ml 1 N HCl are added. Stirring is continued for further 15 seconds.

After 10 minutes centrifugation and washing follow according to Example 1. Magnetic beads are obtained with a size of 1–2 $\mu$m and an iron oxide content of 18.3%.

EXAMPLE 13

100 ml 5% PVAL solution (mean molecular mass 203.000), in which 0.05% polystyrene sulfonic acid and 0.1% polyvinylpyrrolidone is dissolved, are dispersed with 12 ml magnetic colloid according to Example 1 and sonicated for 2 minutes in an ultrasonic bath. Suspension in 2.2 liters vegetable oil, whose composition is analogous to that in Example 12, follows.

After 10 sec stirring, 8 ml 12% glutaraldehyde solution and 20 ml 2.5 N HCl are thereafter added in 10 sec intervals each.

After according washing and preparation as described in Example 1, 2–4 $\mu$m large magnetic particles with a iron oxide content of 7.5% are obtained.

EXAMPLE 14

6.5 ml Ferrofluidics EMG 807 are dispersed in 100 ml polymer phase containing 10% PVAL (mean molecular mass 88.000), 0.05% cellulose acetate butyrate and 0.1% polyvinylpyrrolidone. Sonication for 3 minutes in an ultrasonic bath follows. Thereafter the dispersion is suspended under stirring (stirring speed 2000 rpm) in 2300 ml vegetable oil which contains 1.8% Synperonic L61, 0.2% Tetronic 1101 and 1% Dehymuls FCE.

After 10 sec, 8 ml 12% glutaraldehyde solution containing 20 mol % ethylenediamine and 23 ml 2.5 N HCl are added, within 10 second intervals each. Stirring is contained for another 10 seconds.

After 10 minutes the suspension is separated and washed according to Example 1. We obtain magnetic particles with a bead size distribution of 1–3 $\mu$m and an iron oxide content of 10.4%.

EXAMPLE 15

300 mg of the polymer particles synthesized according to Example 1 are suspended in 10 ml water and 10 ml 3.5 M NaOH as well as 15 ml epichlorohydrin are added. The suspension is vigorously stirred for two hours at 55° C.

Thereafter, the magnetic particles are collected using a neodymium-iron-boron magnet. The product is suspended in 10 ml water and again magnetically separated. This washing separation procedure is repeated 10 times followed by one washing with acetone.

30 mg of the activated magnetic particles are reacted with 2 ml 10% hexamethylenediamine dissolved in a 0.1 M borate buffer, pH 11.4, for 2 hours at 50° C., followed by 10 washing steps with water. The obtained product is afterwards charged with 2 ml 0.1 M potassium phosphate buffer, pH 7.0, in which 12.5% glutaraldehyde is dissolved. The reaction takes place at 30° C. for two hours. The reaction is followed by 10 washing procedures with water over a period of 30 minutes and two washing procedures with 0.1 M potassium phosphate buffer, pH 7.5.

By incubating 0.3 mg streptavidin dissolved in 1 ml 0.1 M potassium phosphate buffer, pH 7.5, over a period of 12 hours at 4° C., 0.11 mg streptavidin is bound to the matrix. Biotinylated DNA fragments can be bound to this matrix according to the known methods for DNA sequencing.

EXAMPLE 16

30 mg of the synthesized and with epichlorohydrin/hexamethylenediamine/glutaraldehyde activated magnetic particles, as described in Example 15, are subjected to a reaction with 0.3 mg anti-insulin-antibody for 24 hours at 4° C., which is dissolved in 2 ml 0.1 M potassium phosphate buffer, pH 7.5. 0.28 mg antibody are bound.

EXAMPLE 17

60 mg magnetic particles according to Example 3 are dehydrated by successive addition of acetone-water mixtures (1:3, 1:1, 3:1) and finally anhydrous acetone. The suspension is dispersed in 2 ml dried dimethyl sulfoxide which contains 0.1% tin octoate and activated by adding 0.5 ml hexamethylenediisocyanate over a period of 30 minutes at 45° C. Subsequently the samples are washed 5 times alternately with a few ml dimethyl sulfoxide and acetone.

30 mg of the activated fraction are reacted with 1 ml anhydrous dimethyl sulfoxide containing 20% polyethylene glycol 400 and 0.05% DABCO for 4 hours at 30° C. The sample is subsequently washed once with dimethyl sulfoxide and 5 times with water followed by a dehydration process with acetone-water mixtures as described above.

The polyethylene glycol coupled fraction is subsequently reacted for 45 minutes at room temperature with 6 mM 4-dimethylaminopyridine and 2-fluoro-1-methylpyridinium-p-toluenesulfonate each dissolved in 1 ml dimethyl sulfoxide. The product is washed 5 times alternately with dimethyl sulfoxide and acetone.

By incubating an anti-thyroxine-antibody solution (0.25 mg antibody/ ml 0.05 M potassium phosphate buffer, pH 7.5) at 4° C. with the activated product, 0.23 mg antibody are subsequently coupled. After several washing steps using the coupling buffer, the residual active groups are deactivated by a 4 hour incubation with 2 ml 0.1 M Tris-HCl buffer solution, pH 8.5, containing 20 mM mercaptoethanol. Thereafter the magnetic particles are rinsed with PBS buffer, pH 7.2.

The coupled magnetic particles can be applied for thyroxine determination according to the known methods.

EXAMPLE 18

30 mg of the fraction activated with hexamethylendiisocyanate according to Example 17 are incubated with 2 ml 0.3 M KOH/methanol solution 1:1 for 5 hours. After the 5 hours reaction period at room temperature, the product is rinsed 5 times with water. The amino group containing fraction is subsequently activated with glutaraldehyde according to Example 15, followed by several washing procedures over a period of 30 minutes.

Incubation of 0.35 mg anti-mouse IgG, dissolved in 1 ml 0.1 M potassium phosphate buffer, pH 7.5, for 20 hours at 4° C., results in 0.28 mg bound IgG.

The coupled product can be used for cell separation according to the known methods.

EXAMPLE 19

30 mg magnetic particles according to Example 10 are incubated at 0° C. with 4 ml water in which 100 mg BrCN is dissolved. By adding 2 N NaOH, the pH is adjusted to 11.5. The reaction is stopped by magnetic separation of the magnetic fraction. The product is washed 4 times with ice-water. One washing step with 0.01 N HCl and 0.1 M bicarboante buffer, pH 8.2 follows.

1 ml 0.1 M bicarbonate buffer, pH 8.2, in which 0.2 mg anti-CD4 antibody is dissolved, is incubated with the activated magnetic beads for 12 hours at 4° C. Several rinsing steps follow with PBS buffer, pH 7.2, which contains 0.5 M NaCl and 0.1% Triton X100. A carrier is obtained onto which 0.18 mg antibody is bound.

The obtained carrier can be applied for isolating T-helper cells.

EXAMPLE 20

30 mg magnetic particles according to Example 5 are activated in the same manner as in Example 19 with BrCN. Coupling of heparin (molecular mass 6000) takes place by incubating 0.5 mg heparin, dissolved in 1 ml bicarbonate buffer, pH 8.2, over a period of 12 hours.

The product is subsequently incubated for 2 hours at room temperature with 0.1 M ethanolamine solution, pH 8.0, and then washed 4 times with 0.1 M acetate buffer, pH 4.

The obtained fraction can be applied to separate anti-thrombin III according to the known methods.

EXAMPLE 21

30 mg magnetic particles according to Example 4 are dehydrated by successive addition of acetone-water mixtures as described above. The magnetic beads are incubated with 1 ml dimethyl sulfoxide each containing 6 mM 4-dimethylaminopyiridine and 5 mM 2-fluoro-1methylpyridinium-p-toluenesulfonate for 45 minutes at room temperature. 5 times alternate washing with acetone and dimethyl sulfoxide as well as one rinsing with 0.05 M potassium phosphate buffer, pH 7.5, follows.

1 ml 0.05 M potassium phosphate buffer, pH 7.5, which contains 0.3 mg protein A, is subsequently added. Coupling takes place over a period of 12 hours at room temperature, followed by several washing procedures with PBS buffer containing 0.5% NaCl and 0.1% Triton X100. 0.27 mg protein are coupled.

The magnetic fraction is used for the separation of IgG-subclasses analogous to the known methods.

EXAMPLE 22

30 mg magnetic particle fraction according to Example 12 are washed once with 2 ml 0.5 M carbonate buffer, pH 11. Subsequent activation with 100 μl divinyl sulfone follows by adding 1 ml wash buffer over a period of 70 minutes at room temperature. The product is rinsed several times with water over a period of 30 minutes.

The magnetic fraction is incubated with 1 ml carbonate buffer, pH 10, in which 10% lactose is dissolved, for 20 hours at room temperature. 0.68 mg lactose are bound.

The carrier can be used for the purification of lectines from misletoe extracts according to the known methodologies.

EXAMPLE 23

30 mg magnetic particles according to Example 7 which were activated with epichlorohydrin, as described in Example 15, are subjected to a reaction with 0.3 M adipic acid dihydrazide in a 0.2 M carbonate buffer, pH 9, over a period of 16 hours at room temperature to form hydrazide derivatives. After several washing steps using 0.1 M Tris-HCl buffer, pH 8.5, residual oxirane groups are quenched by a 4-hour incubation with the wash buffer containing 0.3 M mercaptoethanol. A final washing with 3 ml 0.1 M sodium acetate buffer, pH 5.5, follows.

1 ml acetate wash buffer, in which 0.3 mg anti-HGH (human growth hormon) antibody and 10 mM sodium m-periodate is dissolved, is incubated for 40 minutes at 4° C. in the dark. Subsequently it is rinsed with sodium acetate buffer five times and then washed two times with PBS buffer. 0.21 mg antibody are coupled.

The coupled carrier can be used for the detection of HGH.

EXAMPLE 24

30 mg magnetic particles according to Example 9 are suspended in water and separated using a hand magnet. The separated fraction is incubated with 0.5 ml 0.1 M nitric acid which contains 0.1 M ammonium cerium(IV) nitrate for 15 minutes at room temperature. Subsequently the magnetic particles are separated by magnetic means and washed once with water. The fraction is brought to reaction by incubating 0.5 ml acrylic acid and 0.5 ml hexane for 15 minutes at 50° C. 10 washing procedures follow over a period of 30 minutes. The graft yield amounts to 85%.

The grafted fraction is activated for 30 minutes at room temperature with 1 ml 0.1 M 3-(N-morpholino)propane sulfonic acid (MOPS), pH 7.5, in which 5% 1-cyclohexyl-3-(2-morpholinoethyl) carbodiimide metho-p-tolucnesulfonate is dissolved. The activation is followed by 5 washing steps with ice-water. 0.3 mg anti-LDL (low density lipoprotein) antibody dissolved in 1 ml MOPS buffer, pH 7.5, is added. The reaction continues for 24 hours at 4° C. Afterwards the carrier is deactivated by means of a 4-hour incubation with 5 ml 5 mM ethanolamine/0.1 M Tris-HCl buffer, pH 8.5. 0.25 mg antibody are bound. The coupled matrix can be applied for the removal of LDL from biological fluids.

EXAMPLE 25

30 mg magnetic particles according to Example 3 are grafted with acrylic acid in the same manner as in Example 24. 100 µg oligo(dT)20 are substituted at the 5'-end with ethylenediamine according to the method described in DNA, Vol. 4, 327 (1985). The magnetic particle fraction is incubated with the $NH_2$-substituted oligonucleotide, dissolved in 1 ml 0.1 M imidazole buffer, pH 7.0, for 20 hours at room temperature. This is followed by several washing procedures with the imidazole buffer containing 0.1% Triton X100. 38 µg oligonucleotide are bound. The obtained magnetic particles can be used for the isolation of mRNA according to established methods.

EXAMPLE 26

100 mg magnetic particles according to Example 9 are successively dehydrated with the aid of the acetone-water mixtures as described above. This is followed by an activation using hexamethylenediisocyanate according to Example 17.

The activated particles are incubated with 2 ml dimethyl sulfoxide containing 0.1% tin octoate and 30 mg m-aminophenylboronic acid for 6 hours at 30° C. This is followed by several washing procedures with water.

The boronic acid coupled magnetic carriers can be applied for the detection of glycated hemoglobin in blood according to the established methods.

EXAMPLE 27

2 ml water, in which 50 mg Cibacron Blue F3G-A is dissolved, are charged to 30 mg magnetic particles according to Example 14.

The mixture is reacted for 30 minutes at 60° C. Afterwards 1 ml 25% NaCl solution is added and heating is continued for one further hour at 75° C. After addition of 10% sodium carbonate solution, heating is contained for further two hours at 70° C., followed by several hours of washing with water.

The obtained matrix can be used for the separation of alcohol dehydrogenase according to the known methods.

What is claimed is:

1. A process for the production of spherical magnetic polymer particles comprising polyvinyl alcohol, the process comprising:
    dispersing a magnetic material in colloid form in a polymer phase, said polymer phase comprising an aqueous polyvinyl alcohol solution, wherein the polyvinyl alcohol has reactive hydroxyl groups;
    adding the aqueous polymer phase thus obtained to an organic phase containing a mixture of at least two emulsifiers dissolved therein, and suspending said polymer phase in said organic phase by stirring at room temperature;
    wherein said organic phase is not miscible with the polymer phase, and wherein at least one emulsifier has semi-hydrophilic properties and at least one emulsifier is lipophilic; and
    adding a water-soluble cross-linking agent capable of reacting with said reactive hydroxyl groups of said polyvinyl alcohol while stirring the suspension, thus forming a polymer by cross-linking the reactive hydroxyl groups of the polyvinyl alcohol and incorporating said magnetic material into said polymer and thus forming spherical magnetic polymer particles, wherein the spherical magnetic polymer particles thus obtained range in size from 1–10 µm.

2. A process in accordance with claim 1, wherein the concentration of said mixture of emulsifiers in said organic phase is 2–6 vol. %.

3. A process in accordance with claim 1 wherein 0.01 to 2 weight % of one or more emulsifier is added to the aqueous polyvinyl alcohol solution prior to dispersing the magnetic material in said aqueous polyvinyl alcohol solution.

4. A process in accordance with claim 3 wherein said one or more emulsifier is selected from the group consisting of: proteins, cellulose derivatives, sulfonic acid derivatives, polyvinyl pyrrolidones, polyethylene glycols, and mixtures of these.

5. A process in accordance with claim 1, wherein the polymer phase contains 2.5–12.5 weight % polyvinyl alcohol.

6. A process in accordance with claim 1, wherein the magnetic material in colloid form comprises ferromagnetic or superparamagnetic substances.

7. A process in accordance with claim 1, wherein the concentration of the cross-linking agent is between 2 and 7 vol. %, relative to the aqueous polymer phase.

8. A process in accordance with claim 1, wherein the cross-linking agent is used with the addition of water-soluble diamines.

9. A process in accordance with claim 1 wherein a dialdehyde is used as a cross-linking agent and wherein 20–50 volume % acid is added to the polymer phase.

10. Spherical magnetic polymer particles obtained by the process in accordance with claim 1, wherein said particles comprise reactive hydroxyl groups.

11. Spherical magnetic polymer particles in accordance with claim 10, wherein a plurality of polymer chains are chemically bonded to said reactive hydroxyl groups and wherein said polymer chains comprise polymerized vinyl monomers, said vinyl monomers having one or more carboxyl, hydroxyl, amino, aldehyde or oxirane groups.

12. Spherical magnetic polymer particles according to claims 10 or 11, wherein the polymer particles have surfaces and said surfaces of the polymer particles display a plurality of spacer molecules to which one or more biomolecules can be coupled.

13. Spherical magnetic polymer particles in accordance with claim 12, wherein the biomolecules are coupled to the spacer molecules and the biomolecules are selected from the group consisting of antibodies, peptides, proteins, enzymes, streptavidin, avidin, oligonucleotides, oligosaccharides and DNA fragments.

14. A process according to claim 1, further comprising:

grafting vinyl monomers having one or more functional groups to said spherical magnetic polymer particles by radical polymerization under the catalytic effect of cerium (IV) salts, wherein said functional groups comprise carboxyl, hydroxyl, amino, aldehyde or oxirane groups and wherein the grafting process is performed in the presence of an organic solvent which cannot be mixed with water.

* * * * *